US005621803A

United States Patent [19]

Laak

[11] Patent Number: 5,621,803

[45] Date of Patent: Apr. 15, 1997

[54] ACTIVE ATTENUATION SYSTEM WITH ON-LINE MODELING OF FEEDBACK PATH

[75] Inventor: Trevor A. Laak, Madison, Wis.

[73] Assignee: Digisonix, Inc., Middleton, Wis.

[21] Appl. No.: 591,126

[22] Filed: Jan. 25, 1996

Related U.S. Application Data

[63] Continuation of Ser. No. 300,315, Sep. 2, 1994, abandoned.

[51] Int. Cl.[6] .............................. A61F 2/20; H03B 29/00

[52] U.S. Cl. .............................................................. 381/71

[58] Field of Search .......................................... 381/71, 94

[56] References Cited

U.S. PATENT DOCUMENTS

| | | | |
|---|---|---|---|
| 4,122,303 | 10/1978 | Chaplin et al. . | |
| 4,677,676 | 6/1987 | Eriksson . | |
| 4,677,677 | 6/1987 | Eriksson . | |
| 4,987,598 | 1/1991 | Eriksson . | |
| 5,022,082 | 6/1991 | Eriksson et al. . | |
| 5,033,082 | 7/1991 | Eriksson et al. . | |
| 5,206,911 | 4/1993 | Eriksson et al. . | |
| 5,216,722 | 6/1993 | Popovich . | |
| 5,337,366 | 8/1994 | Eguchi et al. | 381/71 |
| 5,396,561 | 3/1995 | Popovich et al. | 381/71 |

OTHER PUBLICATIONS

"Active Adaptive Sound Control In A Duct: A Computer Simulation", J.C. Burgess, Journal of Acoustic Society of America, 70(3), Sep., 1981, pp. 715–726.

*Primary Examiner*—Curtis Kuntz
*Assistant Examiner*—Ping W. Lee
*Attorney, Agent, or Firm*—Andrus, Sceales, Starke & Sawall

[57] ABSTRACT

In an active adaptive attenuation system having a main model, a second adaptive filter model is provided having an input from the output of the main model, and an output supplied to the input of the main model. A copy of the main model has an input from the input to the second model and an output supplied to a multiplier multiplying the error signal and the output of the copy and supplying the resultant product as a weight update signal to the second model.

3 Claims, 1 Drawing Sheet

ACTIVE ATTENUATION SYSTEM WITH ON-LINE MODELING OF FEEDBACK PATH

This application is a continuation of Ser. No. 08/300,315, filed Sep. 2, 1994, now abandoned.

BACKGROUND AND SUMMARY

The invention relates to active adaptive attenuation systems.

An active adaptive attenuation system has an output transducer outputting a control signal combining with a system input signal to yield a system output signal. An error transducer senses the system output signal and outputs an error signal to an adaptive filter model having a model input from a reference signal correlated to the system input signal, and a model output outputting a correction signal to the output transducer. Active adaptive attenuation systems are particularly useful in cancellation or control of sound and vibration.

The present invention provides a second adaptive filter model having a model input from the correction signal, an error input from the error signal, and a model output supplied to the model input of the first model. The resulting recursive controller is particularly useful as an active adaptive attenuation system since the second model can directly model and compensate for feedback from the output transducer to the input transducer. In one desirable aspect, the invention enables faster convergence of the overall system.

DETAILED DESCRIPTION

Figure 1:
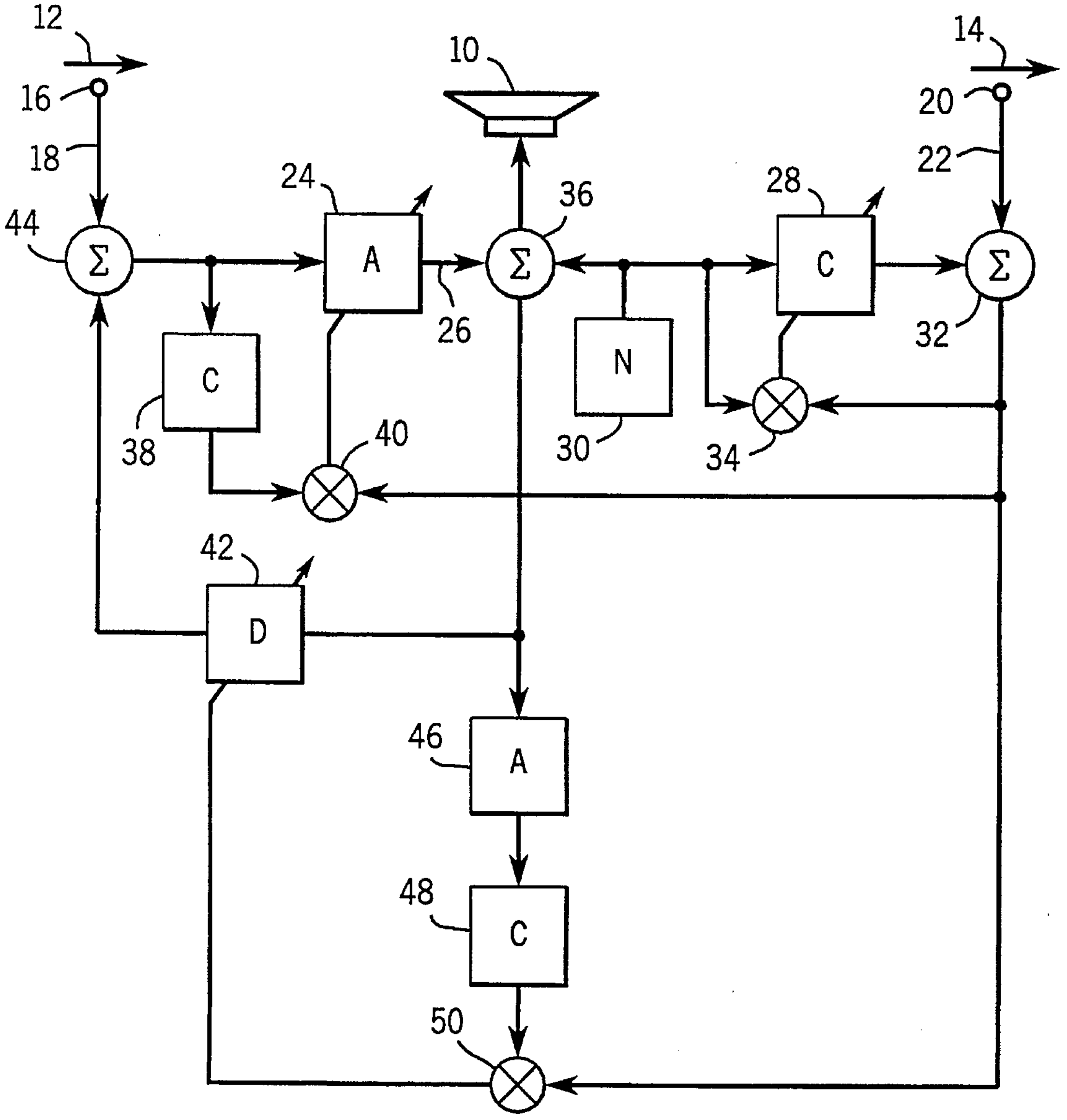
FIG. 1 is a schematic illustration of an active adaptive attenuation system in accordance with the invention.

FIG. 1 shows an active adaptive attenuation system having an output transducer 10, such as a loudspeaker, shaker, or other actuator, outputting a control signal combining with a system input signal 12 to yield a system output signal 14. An input transducer 16, such as a microphone, accelerometer, or other sensor, senses the system input signal and outputs a reference signal 18 correlated thereto. An error transducer 20 senses the system output signal and outputs an error signal 22. An adaptive filter model A at 24 has a model input from the reference signal, an error input from the error signal, and an output outputting a correction signal 26 to the output transducer to minimize the error input, as known in the art, for example U.S. Pat. No. 4,677,676, incorporated herein by reference.

The transfer function from the output of adaptive filter model 24 to error transducer 20 is modeled by an adaptive filter model C at 28, as in the incorporated '676 patent. Filter model C has a model input from an auxiliary random signal source N at 30 providing an auxiliary random signal uncorrelated with the system input signal 12. The output of C model 28 is summed at summer 32 with error signal 22, and the resultant sum is multiplied at multiplier 34 with the input to C model 28, with the resultant output product providing the weight update signal for C model 28. The auxiliary random signal from source 30 is also summed at summer 36 with the output of model 24, and the resultant sum is supplied to output transducer 10. A copy 38 of the C filter model has an input from the input to A filter model 24 and an output supplied to multiplier 40 multiplying the error signal and the output of copy 38 and supplying the resultant product as the weight update signal to A filter model 24, all as in the incorporated '676 patent.

In the present invention, an adaptive filter model D at 42 has a model input from the correction signal, an error input from the error signal, and a model output summed at summer 44 with reference signal 18 and supplied to the input of A filter model 24. A copy 46 of the A filter model and a copy 48 of the C filter model are connected in series and have an input from the input to D filter model 42, and an output supplied to a multiplier 50 multiplying the error signal and the output of such copies and supplying the resultant product as the weight update signal to D filter model 42.

The feedback path from output transducer 10 to input transducer 16 is modeled on-line during modeling of the feedforward path by main model 24. The input to D model 42 is provided by the output of summer 36 which is the sum of correction signal 26 and the auxiliary random signal from auxiliary random signal source 30. In an alternate embodiment, C model 28 and/or D model 42 may be pre-modeled off-line before model 24 is brought on-line. In this latter embodiment, C model 28 and/or D model 42 are partially converged when main model 24 is brought on-line, and continue to adapt when model 24 is adapting on-line. In both embodiments, each of models 24, 28 and 42 actively adapts during active adaptive on-line operation of the other models.

In the disclosed embodiment, each of A filter model 24, C filter model 28 and D filter model 42 is an FIR (finite impulse response) filter, such as an LMS (least mean square) filter. The combination of filters A and D provides a recursive filter. In other embodiments, one or more of filters 24, 28, 42 may be IIR (infinite impulse response) filters, such as RLMS (recursive least mean square) filters. In the case of a periodic system input signal 12, the reference signal 18 may be provided by one or more error signals, "Active Adaptive Sound Control In A Duct: A Computer Simulation", J. C. Burgess, Journal of Acoustic Society of America, 70(3), September 1981, pages 715–726, U.S. Pat. Nos. 5,206,911, 5,216,722, incorporated herein by reference.

It is recognized that various equivalents, alternatives and modifications are possible within the scope of the appended claims.

I claim:

1. An active adaptive attenuation system having an output transducer outputting a control signal combining with a system input signal to yield a system output signal, an error transducer sensing said system output signal and outputting an error signal, a first adaptive filter model having a model input from a reference signal correlated to said system input signal, an error input from said error signal, and a model output outputting a correction signal to said output transducer to introduce said control signal to minimize said error input, a second adaptive filter model having a model input from said correction signal, an error input from said error signal, and a model output also supplied to said model input of said first model, wherein each model actively adapts during active adaptive on-line operation of the other model, a third adaptive filter model having a model input and having a model output summed with said error signal and modeling the transfer function from the output of said first adaptive filter model to said error transducer, an auxiliary signal source supplying an auxiliary signal to said output transducer and to the model inputs of each of said second and third models, such that said auxiliary signal is filtered by said second adaptive filter model and supplied to the model input of said first model.

2. The invention according to claim 1 comprising a series connection of a copy of said first adaptive filter model and a copy of said third adaptive filter model, said series connection having an input from the output of said first adaptive filter model and also from said auxiliary signal source, said series connection having an output supplied to a multiplier multiplying said error signal and the output of said series connection and supplying the resultant product as a weight update signal to said second adaptive filter model.

3. The system according to claim 1 comprising a summer summing the output of said first adaptive filter model and said auxiliary signal from said auxiliary signal source and supplying the resultant sum to said output transducer and to the input of said second adaptive filter model.

* * * * *